United States Patent
He et al.

(10) Patent No.: US 11,945,774 B2
(45) Date of Patent: Apr. 2, 2024

(54) BIMETALLIC COORDINATION METAL-ORGANIC FRAMEWORK MATERIAL, PREPARING METHOD THEREOF, AND APPLICATION THEREOF

(71) Applicants: GUANGDONG UNIVERSITY OF TECHNOLOGY, Guangzhou (CN); CITY UNIVERSITY OF HONG KONG, Hong Kong (CN)

(72) Inventors: Jun He, Guangzhou (CN); Jieying Hu, Guangzhou (CN); Liangming Tang, Guangzhou (CN); Zhiqing Liu, Guangzhou (CN); Xinhe Ye, Guangzhou (CN); Gengyuan Zhang, Guangzhou (CN); Zhengtao Xu, Guangzhou (CN)

(73) Assignees: GUANGDONG UNIVERSITY OF TECHNOLOGY, Guangzhou (CN); CITY UNIVERSITY OF HONG KONG, Hong Kong (HK)

( * ) Notice: Subject to any disclaimer, the term of this patent is extended or adjusted under 35 U.S.C. 154(b) by 0 days.

(21) Appl. No.: 18/109,843

(22) Filed: Feb. 14, 2023

(65) Prior Publication Data
US 2023/0286894 A1   Sep. 14, 2023

(30) Foreign Application Priority Data
Feb. 15, 2022   (CN) .......................... 202210137451.4

(51) Int. Cl.
*C07C 51/41*   (2006.01)
(52) U.S. Cl.
CPC .................. *C07C 51/418* (2013.01)

(58) Field of Classification Search
CPC ........ C07C 51/418; C07F 15/04; C07F 15/06; C07F 7/22; C07F 7/24
See application file for complete search history.

(56) References Cited

FOREIGN PATENT DOCUMENTS

| CN | 105175295 A | * 12/2015 | .............. B01J 20/22 |
| CN | 109265702 A | 1/2019 | |

(Continued)

OTHER PUBLICATIONS

CN 105175295, Luo Xubiao et al., Preparation for thiol-functionalization of MOFs material and application thereof in adsorption and removal of heavy metal ions in water, English translation, 10 pages (Year: 2015).*

*Primary Examiner* — Yate' K Cutliff
(74) *Attorney, Agent, or Firm* — Georgi Korobanov

(57) ABSTRACT

The present disclosure provides a bimetallic coordination metal-organic framework material, a preparing method thereof, and an application thereof. In the bimetallic coordination metal-organic framework material, carboxyl groups and soft groups of ligands are coordinated with coordination metal ions to assemble a structure having space and functions divided into covalent charge carrier layers and charge storage ion layers. Further, through the conjugation effect, the bimetallic coordination metal-organic framework material has unique electromagnetic properties, good electrical conductivity, and magnetic coupling performance. Thus, the bimetallic coordination metal-organic framework material is used as superconducting materials, conductive materials, semiconductor materials, or electromagnetic materials. Through the preparing method, the structure including the covalent charge carrier layers and the charge storage ion layers is assembled, so the bimetallic coordination metal-organic framework material has unique electromagnetic properties.

9 Claims, 6 Drawing Sheets

(56) References Cited

FOREIGN PATENT DOCUMENTS

| CN | 111153841 | A | 5/2020 |
| CN | 113477220 | A | 10/2021 |
| JP | 2007063448 | A | 3/2007 |

* cited by examiner

BIMETALLIC COORDINATION METAL-ORGANIC FRAMEWORK MATERIAL, PREPARING METHOD THEREOF, AND APPLICATION THEREOF

TECHNICAL FIELD

The present disclosure relates to a technical field of metal-organic frameworks materials, and in particular to a bimetallic coordination metal-organic framework material, a preparing method thereof, and an application thereof.

BACKGROUND

Coordination polymers (CPs) are infinite chain structures or infinite network structures in one-dimension, two-dimension, or three-dimension. Metal ions, or metal groups and organic ligands form the coordination polymers through coordination bonds. Porous coordination polymers, i.e. metal-organic framework (MOF) materials, have been rapidly developed in the last 30 years, and structures, properties, and functions thereof are designed and adjusted by changing various organic ligands, metal centers, and topologies, thus releasing potential applications of the MOFs in catalysis, sensing, gas storage, and separation. However, due to relatively long distance between the metal centers, reported three-dimensional porous coordination polymers exhibit extremely low electrical conductivity and weak magnetic coupling performance.

By designs of the ligands, highly symmetrical sulfhydryl conjugated ligands, such as hexamercaptobenzene and hexamercaptotritylbenzene, are synthesized with transition metals to form two-dimensional coordination polymers, which generally exhibit zero band gap and good electrical conductivity. DAOBEN ZHU and members of his group prepare a two-dimensional coordination polymer (Cu-BHT) based on the hexamercaptobenzene and copper, and exceptional electromagnetic properties of the Cu-BHT is confirmed by a zero resistivity measurement, an alternating current (AC) magnetization measurement, and a specific heat measurement. The prepared Cu-BHT exhibits superconductivity at about 0.25 K. Further, an antimagnetic transition of the prepared Cu-BHT occurred at about 3 K, indicating an existence of a second superconducting phase related to monolayer or multilayer of Cu-BHT, which is the first time that superconductivity is observed in the coordination polymers.

Therefore, it is highly challenging to synthesize a porous coordination polymer with high electrical conductivity and exceptional magnetic properties.

SUMMARY

In order to overcome defects in the prior art, a first object of the present disclosure is to provide a bimetallic coordination metal-organic framework material. Through a design of ligands, the bimetallic coordination metal-organic framework material has two different metal coordination structures, a first one of which is a two-dimensional coordination network structure formed by coordination of metal and the ligands, and a second one of which is a zero-dimensional coordination structure, a one-dimensional coordination structure, or a two-dimensional coordination structure embedded between the two-dimensional coordination network structure, so that the bimetallic coordination metal-organic framework material has special magnetic properties and high electrical conductivity.

A second object of the present disclosure is to provide a preparing method for the bimetallic coordination metal-organic framework material.

A third object of the present disclosure is to provide an application for the bimetallic coordination metal-organic framework material.

To achieve the first object, the present disclosure provides the bimetallic coordination metal-organic framework material. The bimetallic coordination metal-organic framework material comprises an M1 two-dimensional coordination network structure including M1 coordination layers and M2 coordination structures embedded between the M1 coordination layers. Coordination metal ions M1 are coordinated with ligands to form the M1 two-dimensional coordination network structure. Each of the M2 coordination structures is a zero-dimensional M2 coordination structure, a one-dimensional M2 coordination structure, or a two-dimensional M2 coordination structure. Coordination metal ions M2 are coordinated with the ligands to form the M2 coordination structures.

The coordination metal ions M1 are coordinated with the ligands to form the M1 coordination layers and the M1 coordination layers are assembled into the M1 two-dimensional coordination network structure, which is functioned as a carrier layer configured for charge transport. Meanwhile, the coordination metal ions M2 are coordinated with the ligands to from zero-dimensional M2 coordination structures, one-dimensional M2 coordination structures, or two-dimensional M2 coordination structures embedded between the M1 coordination layers, which have ionic properties, and are acted as ion layers configured for charge storage. Therefore, a formation of the carrier layer and the ion layers through bimetallic coordination of metal-organic framework material makes the bimetallic coordination metal-organic framework material have special electromagnetic properties.

Furthermore, each of the ligands is a compound containing a carboxyl group and soft groups. The coordination metal ions M1 form a M1 two-dimensional coordination network structure with the soft groups or form the M1 two-dimensional coordination network structure with the soft groups and carboxyl groups of the ligands. The coordination metal ions M2 and oxygen atoms of the carboxyl groups of the ligands form the M2 coordination structures embedded between the M1 coordination layers.

The soft groups are —XH, and X is selected from S and Se.

When the coordination metal ions M1 are coordinated with the soft groups of the ligands to form the M1 two-dimensional coordination network structure, the coordination metal ions M2 are coordinated with the oxygen atoms of the carboxyl groups of the ligands to form the M2 coordination structures embedded between the M1 coordination layers.

When the coordination metal ions M1 are coordinated with the soft groups and the carboxyl groups of the ligands to form the M1 two-dimensional coordination network structure, each of the coordination metal ions M1 is simultaneously coordinated with the soft groups and an oxygen atom of the carboxyl group of each of the ligands. Each of the coordination metal ions M2 is coordinated with another oxygen atom of the carboxyl group of each of the ligands to form one M2 coordination structure embedded between each two adjacent M1 coordination layers.

Groups containing S and Se are the soft groups. When S and Se are coordinated with the coordination metal ions M1, positions of the ligands and the coordination metal ions M1 are adjusted through coordination bonds, making a distance between each two adjacent coordination metal ions M1 close and forming a two-dimensional coordination network structure, which in turn improves electrical conductivity and weak magnetic coupling of the bimetallic coordination metal-organic framework material. Meanwhile, the oxygen atoms of each carboxyl group are protruding on two sides, and the oxygen atoms on one side are coordinated by bonding with two top positions of a group of the coordination metal ions M2, forming one coordination network structure embedded between edges of each two adjacent M1 coordination layers, i.e., each two adjacent M1 coordination layers share one coordination network structure. The M2 coordination structures are functioned as the ion layers; thus, the soft groups are bonded with the coordination metal ions M1 to form the M1 two-dimensional coordination network structure including the M1 coordination layers. The M1 two-dimensional coordination network structure is acted as covalent charge carrier layers, and the M2 coordination structures are acted as charge storage ion layers, so that the bimetallic coordination metal-organic framework material has the special electromagnetic properties.

Furthermore, the M2 coordination structures comprise one or more of $H_2O$, hydroxide, and halogen.

Furthermore, the coordination metal ions M1 are same as or different from the coordination metal ions M2. The coordination metal ions M1 and the coordination metal ions M2 are selected from one or more of transition metal ions, Ga, In, Sn, Tl, Pb, and Bi.

The transition metal ions and part of a main group of metal ions are configured to construct the bimetallic coordination metal-organic framework material with the ligands, so that the bimetallic coordination metal-organic framework material has the electromagnetic properties. The main group metal ions are Ga, In, Sn, Tl, Pb, and Bi.

The coordination metal ions M1 are the same as or different from the coordination metal ions M2, i.e., the coordination metal ions of bimetallic coordination are the same or different. When the coordination metal ions M1 are the same as the coordination metal ions M2, the coordination metal ions M1 and the coordination metal ions M2 are same monometal, same binary metal, or same plural metal. When the coordination metal ions M1 are different from the coordination metal ions M2, the coordination metal ions M1 and the coordination metal ions M2 are different monometals, different binary metals, or different plural metals. Alternatively, the coordination metal ions M1 and the coordination metal ions M2 are unable to be the monometal, the binary metal, or the plural metal at the same time.

Optionally, the coordination metal ions M1 and the coordination metal ions M2 are selected from one or more of Co, Ni, Fe, Cu, and Mn.

Optionally, the transition metal ions are metal ions of group VIIB, group VIII and group D3. Further, the transition metal ions are Fe, Co, Ni, Cu, and Mn. Furthermore, the transition metal ions are metal ions of group VIII. Moreover, the transition metal ions are Fe, Co, and Ni.

Optionally, the coordination metal ions M1 and the coordination metal ions M2 are monometal selected from one of Co, Ni, and Fe. Alternatively, the coordination metal ions M1 and the coordination metal ions M2 are the binary metal selected from one of NiFe, CoFe, and CoNi. Alternatively, the coordination metal ions M1 and the coordination metal ions M2 are ternary metal such as FeCoNi.

Furthermore, the ligands are an aromatic compound. The carboxyl groups and the soft groups of each of the ligands are directly or indirectly connected to an aromatic ring.

The aromatic compound is a good ligand for constructing the metal-organic framework. The carboxyl group and the soft groups of each of the ligands are connected to the aromatic ring thereof. Through n-conjugation of each aromatic ring, a π-electron highly delocalization structure is formed for charge transport. Each aromatic ring, as a rigid group structure, is attached to at least one corresponding carboxyl group, which is also a rigid group, so a spatial position of a corresponding coordination metal ion is controlled by limiting a spatial position of the oxygen atoms in the corresponding carboxyl group. Further, the oxygen atoms protruding from two sides of the corresponding carboxyl group is coordinated with each of the coordination metal ions M2 to form each of the M2 coordination structures embedded between the M1 coordination layers. The M2 coordination structures act as the charge storage ion layer.

Furthermore, each of the ligands comprises at least one carboxyl group and at least two soft groups.

Optionally, the aromatic compound is selected from a benzene derivative, a naphthalene derivative, and a biphenyl derivative.

Optionally, the aromatic compound may be the benzene derivative having a structure of formula I.

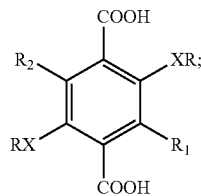

Formula I

Where X is selected from S or Se; R is selected from H or D; and $R_1$ and $R_2$ are separately selected from any one of H, OH, SH, SeH, $CF_3$, the halogen, $C_1$-$C_{10}$ straight-chain alkanes, and $C_1$-$C_{10}$ branched alkanes.

Optionally, the aromatic compound may be the naphthalene derivative having a structure of formula II.

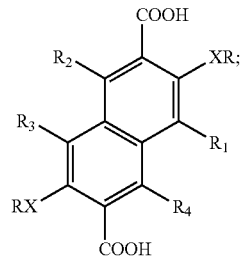

Formula II

Where X is selected from S or Se; R is selected from H or D; and $R_1$, $R_2$ and $R_3$ are separately selected from any one of H, OH, SH, SeH, $CF_3$, the halogen, $C_1$-$C_{10}$ straight-chain alkanes, and $C_1$-$C_{10}$ branched alkanes.

Optionally, the aromatic compound may be the biphenyl derivative having a structure of formula III.

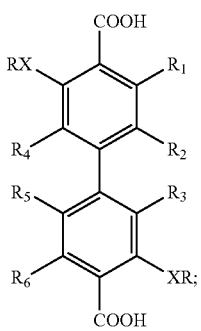

Where X is selected from S or Se, R is selected from H or D; and $R_1$, $R_2$, $R_3$, $R_4$, $R_5$, and $R_6$ are separately selected from any one of H, OH, SH, SeH, $CF_3$, the halogen, $C_1$-$C_{10}$ straight-chain alkanes, and $C_1$-$C_{10}$ branched alkanes.

Optionally, each of the ligands is selected from

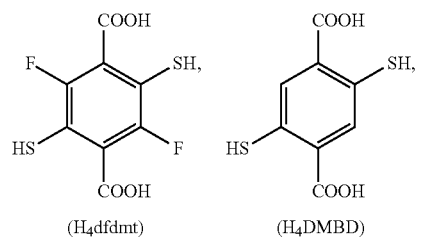

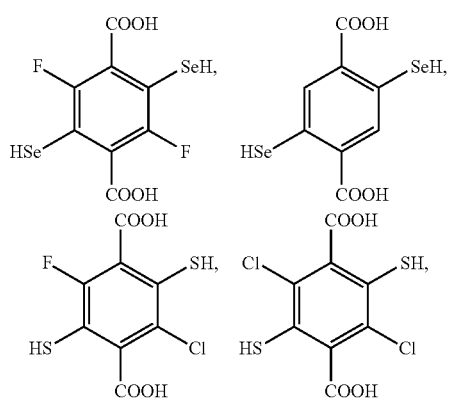

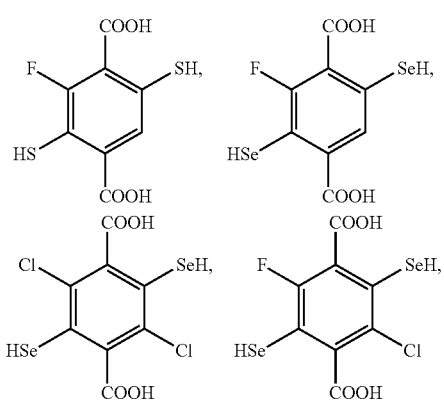

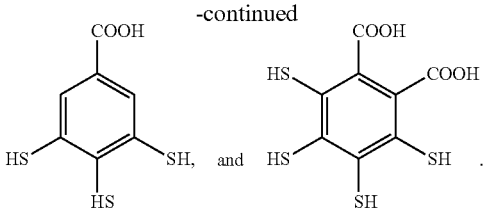

To achieve the second object, the present disclosure provides the preparing method for the bimetallic coordination metal-organic framework material.

The preparing method for the bimetallic coordination metal-organic framework material comprises following steps:

S11: weighing the ligands and metal salt and adding the ligands and the metal salt into a container;

S12: adding a mixed solution of water and an organic solvent into the container, and sealing the container; and S13: placing the container in an oven and heating to obtain the bimetallic coordination metal-organic framework material.

Furthermore, the container is a sealable container. Optionally, the container is a glass tube that is able to be sealed by a hydroxide flame.

Furthermore, replacing the metal salt in the step S11 with a metal oxide. The preparing method further comprises steps of preparing a metal oxide suspension:

S21: dissolving the metal salt in the water to obtain a solution A, and dissolving NaBH4 in the water to obtain a solution B; then adding the solution B into the solution A for reaction, and centrifuging, washing, and vacuum drying a product after reaction to obtain a metal oxide nanosheet; and S22: dispersing the metal oxide nanosheet prepared in the step S21 in the water to obtain the metal oxide suspension.

Optionally, the container is a reaction kettle. When preparing the bimetallic coordination metal-organic framework material, the ligands are weighed and added into the reaction kettle together with the mixed solution containing the water and the organic solvent. The metal oxide suspension prepared in the step S22 is added into the reaction kettle, and a solvothermal reaction is performed to obtain the bimetallic coordination metal-organic framework material.

Further, the metal salt is selected from metal chloride salt, metal nitrate, metal sulfate.

Optionally, a reaction temperature is 60-180° C. and a reaction time is 1-120 h. Furthermore, the reaction temperature is 100-150° C. and the reaction time is 24-96 h. Moreover, the reaction temperature is 120° C. and the reaction time is 72 h.

Optionally, in the mixed solution containing the water and the organic solvent, a volume ratio of the organic solvent to the water is 1: 2-8.

Optionally, the organic solvent is one-component solvent or mixed organic solvent. The organic solvent is selected from one or more of DMF, DEF, and EtOH.

Optionally, when the mixed solution containing the water and the organic solvent is added, a regulator is simultaneously added; and the regulator is selected from one or more of formic acid, acetic acid, and trifluoroacetic acid.

Optionally, a molar ratio of the ligands to metal ions of the metal salt is 1: 2.5-4.

To achieve the second object, the present disclosure provides the application of the bimetallic coordination metal-organic framework material.

In the application of the bimetallic coordination metal-organic framework material, the bimetallic coordination metal-organic framework material is applied in superconducting materials, conductive materials, semiconductor materials, or electromagnetic materials.

Compared with the prior art, in the present disclosure, the bimetallic coordination metal-organic framework material comprises the M1 two-dimensional coordination network structure including the M1 coordination layers and the M2 coordination structures embedded between the M1 coordination layers. The coordination metal ions M1 are coordinated with the ligands to form the M1 two-dimensional coordination network structure. Each of the M2 coordination structures is the zero-dimensional M2 coordination structure, the one-dimensional M2 coordination structure, or the two-dimensional M2 coordination structure. The coordination metal ions M2 are coordinated with the ligands to form the M2 coordination structures. The M1 two-dimensional coordination network structure and the M2 coordination structures are assembled to form a structure having space and functions divided into the covalent charge carrier layers and the charge storage ion layers, so that the bimetallic coordination metal-organic framework material has the special electromagnetic properties.

The soft groups and the carboxyl groups of the ligands are coordinated with the coordination metal ions, the centers of the coordination metal ions are relatively close to each other, and the conjugate effect enhances an electronic coupling effect between adjacent covalent charge carrier layer and charge storage ion layer, so that the bimetallic coordination metal-organic framework material has good conductivity and good magnetic coupling performance.

In the preparing method for the bimetallic coordination metal-organic framework material of the present disclosure, use of a solvothermal method or a template method overcomes a problem that coordination groups of the ligands are too close to assemble the structure having space and the functions divided into the covalent charge carrier layers and the charge storage ion layers, or the coordination groups in the ligands are too far away to form effective interactions between different metal coordination layers, so the preparing method makes the bimetallic coordination metal-organic framework material to have good electromagnetic properties.

The bimetallic coordination metal-organic framework material has good electromagnetic properties, so the bimetallic coordination metal-organic framework material is applied in superconducting materials, conductive materials, semiconductor materials, or electromagnetic materials.

DETAILED DESCRIPTION

Figure 1:
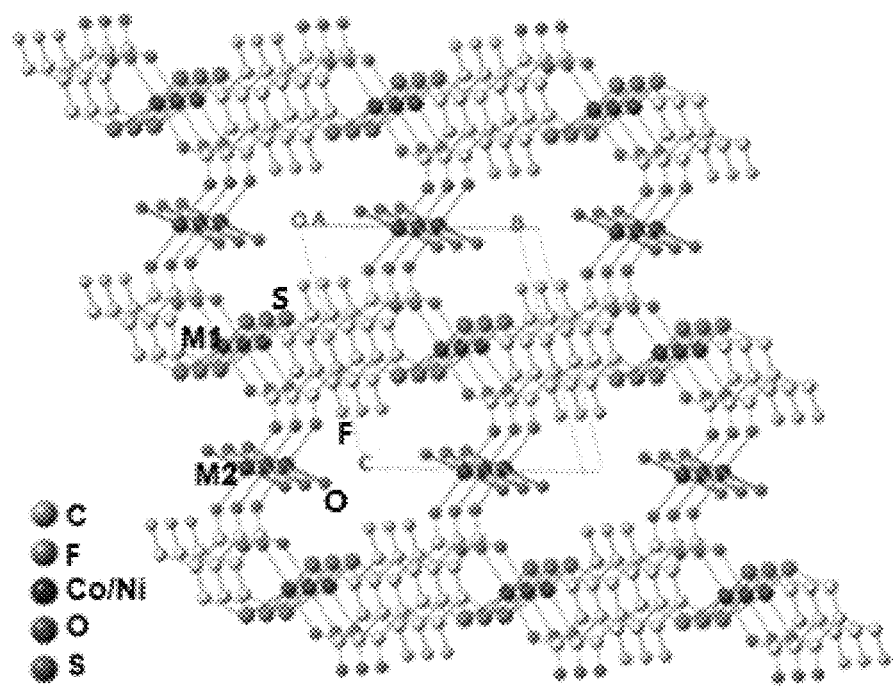
FIG. 1 is a schematic diagram of a bimetallic coordination metal-organic framework material in an embodiment 6 of the present disclosure.

The present disclosure will be further described in conjunction with accompanying drawings and specific embodiments.

Embodiment 1

Ligands, metal chlorinated salt are weighed and added into a container. Then a mixed solution containing N,N-Dimethylformamide (DMF) and water are added into the container. Mixture in the container is uniformly mixed through ultrasound and then is heated in an oven to obtain black powder. After cooling, a black sold product is collected by centrifugation and the black solid product is washed with DMF, the water, and ethanol (EtOH) for several times, then the black solid product is dried in a vacuum drying oven to obtain the bimetallic coordination metal-organic framework material.

Embodiment 2

Synthesis of CoNi-DMBD: H4DMBD (0.0188 mmol), nickel chloride hexahydrate (0.0211 mmol), and cobalt chloride hexahydrate (0.0211 mmol) are weighed and added into a glass tube (with an outer diameter of 10 mm and an inner diameter of 8 mm). Then 0.2 mL of DMF and 0.8 mL of water are added into the glass tube, and the glass tube is sealed with a hydroxide flame, Mixture in the glass tube is uniformly mixed through ultrasound and then is heated in the oven at 120° C. for 72 h to obtain black powder. After cooling, the glass tube is opened, a black sold product is collected by centrifugation and the black solid product is washed with DMF, the water, and EtOH for several times, then the black solid product is dried in a vacuum drying oven at 60° C. to obtain the bimetallic coordination metal-organic framework material. H4DMBD is 2,5-Dimercapto-1,4-benzenedicarboxylic acid.

Embodiment 3

Synthesis of Fe-dfdmt: H4dfdmt (0.0188 mmol) and Ferric chloride hexahydrate (0.0376 mmol) are weighed and added into the glass tube (with the outer diameter of 10 mm and the inner diameter of 8 mm). Then 0.3 mL of DMF and 0.8 mL of water are added into the glass tube, and the glass tube is sealed with the hydroxide flame, Mixture in the glass tube is uniformly mixed through ultrasound and then is heated in the oven at 60° C. for 120 h to obtain black powder. After cooling, the glass tube is opened, a black sold product is collected by centrifugation and the black solid product is washed with DMF, the water, and EtOH for several times, then the black solid product is dried in the vacuum drying oven at 60° C. to obtain the bimetallic coordination metal-organic framework material. H4dfdmt is 2,5-Difluoro-3,6-dimercapto-1,4-benzenedicarboxylic acid.

Embodiment 4

Synthesis of Co-DMBD: $H_4DMBD$ (0.0188 mmol) and cobalt chloride hexahydrate (0.0752 mmol) are weighed and added into the glass tube (with the outer diameter of 10 mm and the inner diameter of 8 mm). Then 0.1 mL of DMF, 0.1 mL of N,N-diethylformamide (DEF), and 1.6 mL of water are added into the glass tube, and the glass tube is sealed with the hydroxide flame. Mixture in the glass tube is uniformly mixed through ultrasound and then is heated in the oven at 100° C. for 96 h to obtain black powder. After cooling, the glass tube is opened, a black sold product is collected by centrifugation and the black solid product is washed with DMF, the water, and EtOH for several times, then the black solid product is dried in the vacuum drying oven at 60° C. to obtain the bimetallic coordination metal-organic framework material.

Embodiment 5

Synthesis of Ni-dfdmt: H4dfdmt (0.0188 mmol) and nickel chloride hexahydrate (0.0564 mmol) are weighed and added into the glass tube (with the outer diameter of 10 mm and the inner diameter of 8 mm). Then 0.2 mL of DMF, 0.1 mL of DEF, and 1.2 mL of water are added into the glass tube, and the glass tube is sealed with the hydroxide flame. Mixture in the glass tube is uniformly mixed through ultrasound and then is heated in the oven at 150° C. for 24 h to obtain black powder. After cooling, the glass tube is opened, a black sold product is collected by centrifugation and the black solid product is washed with DMF, the water, and EtOH for several times, then the black solid product is dried in the vacuum drying oven at 60° C. to obtain the bimetallic coordination metal-organic framework material.

Embodiment 6

Synthesis of CoNi-dfdmt: H4dfdmt (0.0188 mmol), nickel chloride hexahydrate (0.0376 mmol), and cobalt chloride hexahydrate (0.0188 mmol) are weighed and added into the glass tube (with the outer diameter of 10 mm and the inner diameter of 8 mm). Then 0.1 mL of DMF, 0.2 mL of DEF, and 1.2 mL of water are added into the glass tube, and the glass tube is sealed with the hydroxide flame. Mixture in the glass tube is uniformly mixed through ultrasound and then is heated in the oven at 150° C. for 24 h to obtain black powder. After cooling, the glass tube is opened, a black sold product is collected by centrifugation and the black solid product is washed with DMF, the water, and EtOH for several times, then the black solid product is dried in the vacuum drying oven at 60° C. to obtain the bimetallic coordination metal-organic framework material.

Embodiment 7

Synthesis of Ni-DMBD: $H_4DMBD$ (0.0188 mmol) and nickel chloride hexahydrate (0.0422 mmol) are weighed and added into the glass tube (with the outer diameter of 10 mm and the inner diameter of 8 mm). Then 0.2 mL of DEF and 1.2 mL of water are added into the glass tube, and the glass tube is sealed with the hydroxide flame. Mixture in the glass tube is uniformly mixed through ultrasound and then is heated in the oven at 180° C. for 1 h to obtain black powder. After cooling, the glass tube is opened, a black sold product is collected by centrifugation and the black solid product is washed with DMF, the water, and EtOH for several times, then the black solid product is dried in the vacuum drying oven at 60° C. to obtain the bimetallic coordination metal-organic framework material.

Embodiment 8

Synthesis of NiFe-DMBD: $H_4DMBD$ (0.0188 mmol), nickel chloride hexahydrate (0.0211 mmol), and ferric chloride hexahydrate (0.0422 mmol) are weighed and added into the glass tube (with the outer diameter of 10 mm and the inner diameter of 8 mm). Then 0.3 mL of DMF and 0.9 mL of water are added into the glass tube, and the glass tube is sealed with the hydroxide flame, Mixture in the glass tube is uniformly mixed through ultrasound and then is heated in the oven at 120° C. for 72 h to obtain black powder. After cooling, the glass tube is opened, a black sold product is collected by centrifugation and the black solid product is washed with DMF, the water, and EtOH for several times, then the black solid product is dried in the vacuum drying oven at 60° C. to obtain the bimetallic coordination metal-organic framework material.

Embodiment 9

Synthesis of CoFe-DMBD: $H_4DMBD$ (0.0188 mmol), cobalt chloride hexahydrate (0.0376 mmol), and ferric chloride hexahydrate (0.0211 mmol) are weighed and added into the glass tube (with the outer diameter of 10 mm and the inner diameter of 8 mm). Then 0.3 mL of DEF and 0.9 mL of water are added into the glass tube, and the glass tube is sealed with the hydroxide flame. Mixture in the glass tube is uniformly mixed through ultrasound and then is heated in the oven at 120° C. for 72 h to obtain black powder. After cooling, the glass tube is opened, a black sold product is collected by centrifugation and the black solid product is washed with DMF, the water, and EtOH for several times, then the black solid product is dried in the vacuum drying oven at 60° C. to obtain the bimetallic coordination metal-organic framework material.

Embodiment 10

Synthesis of Fe-DMBD: $H_4DMBD$ (0.0188 mmol) and ferric chloride hexahydrate (0.0211 mmol) are weighed and added into the glass tube (with the outer diameter of 10 mm and the inner diameter of 8 mm). Then 0.3 mL of DEF and 0.9 mL of water are added into the glass tube, and 50 μl of acetic acid and is added into the glass tube. The glass tube is sealed with the hydroxide flame. Mixture in the glass tube is uniformly mixed through ultrasound and then is heated in the oven at 120° C. for 72 h to obtain black powder. After cooling, the glass tube is opened, a black sold product is collected by centrifugation and the black solid product is washed with DMF, the water, and EtOH for several times, then the black solid product is dried in the vacuum drying oven at 60° C. to obtain the bimetallic coordination metal-organic framework material.

Embodiment 11

Synthesis of Co-dfdmt: $H_4DMBD$ (0.0188 mmol) and cobalt chloride hexahydrate (0.0211 mmol) are weighed and added into the glass tube (with the outer diameter of 10 mm and the inner diameter of 8 mm). Then 0.2 mL of DEF and 1.3 mL of water are added into the glass tube, and the glass tube is sealed with the hydroxide flame. Mixture in the glass tube is uniformly mixed through ultrasound and then is heated in the oven at 120° C. for 72 h to obtain black powder. After cooling, the glass tube is opened, a black sold product is collected by centrifugation and the black solid product is washed with DMF, the water, and EtOH for several times, then the black solid product is dried in the vacuum drying oven at 60° C. to obtain the bimetallic coordination metal-organic framework material.

Embodiment 12

Synthesis of FeCoNi-dfdmt: H4dfdmt (0.0188 mmol), cobalt chloride hexahydrate (0.0141 mmol), nickel chloride hexahydrate (0.141 mmol), and ferric chloride hexahydrate (0.0141 mmol) are weighed and added into the glass tube (with the outer diameter of 10 mm and the inner diameter of 8 mm). Then 0.3 mL of DEF and 1.4 mL of water are added into the glass tube, and the glass tube is sealed with the hydroxide flame. Mixture in the glass tube is uniformly mixed through ultrasound and then is heated in the oven at 120° C. for 72 h to obtain black powder. After cooling, the glass tube is opened, a black sold product is collected by centrifugation and the black solid product is washed with DMF, the water, and EtOH for several times, then the black solid product is dried in the vacuum drying oven at 60° C. to obtain the bimetallic coordination metal-organic framework material.

Embodiment 13

Synthesis of NiFe-dfdmt: H4dfdmt (0.0188 mmol), cobalt chloride hexahydrate (0.0211 mmol), and ferric chloride hexahydrate (0.0211 mmol) are weighed and added into the glass tube (with the outer diameter of 10 mm and the inner diameter of 8 mm). Then 0.3 mL of DEF and 1.1 mL of water are added into the glass tube, and 25 µl of formic acid and is added into the glass tube. The glass tube is sealed with the hydroxide flame. Mixture in the glass tube is uniformly mixed through ultrasound and then is heated in the oven at 120° C. for 72 h to obtain black powder. After cooling, the glass tube is opened, a black sold product is collected by centrifugation and the black solid product is washed with DMF, the water, and EtOH for several times, then the black solid product is dried in the vacuum drying oven at 60° C. to obtain the bimetallic coordination metal-organic framework material.

Embodiment 14

Synthesis of CoNi-DMBD: 0.004 mol of $Co(NO_3)_2$-$6H_2O$ is dissolved in 50.0 mL of water to obtain a solution A, and 0.005 mol NaBH4 is dissolved in 20 mL of water to obtain a solution B. The solution A is stirred continuously for 10 min to completely dissolve $Co(NO_3)_2$-$6H_2O$, and then the solution B is added into the solution A drop by drop. After 5 min, a mixed solvent is centrifuged to obtain a product, and the product is washed 3 times with the ethanol, and is finally dried under vacuum at room temperature for 5 h. Nickel oxide is prepared according to the process set forth, but $Co(NO_3)_2$-$6H_2O$ is replaced with Ni(NO 3) 2-$6H_2O$.

10 mg of prepared cobalt oxide and 10 mg of prepared nickel oxide are weighed and dispersed in 2.0 mL of water by ultrasound and are stir for 15 min to obtain a metal oxide suspension.

15 mg of $H_4DMBD$ is dissolved in a mixed solution containing 0.25 mL of DMF, 0.5 mL of water, and 0.25 mL of ethanol that is received in a reaction kettle. The reaction kettle is a sealed polytetrafluoroethylene-lined stainless steel reaction kettle. Then the metal oxide suspension is slowly added into the reaction kettle. The reaction kettle is placed in the oven and the solvent heat reaction is performed at 120° C. for 72 h. A final product is washed with methanol for several times and then dried under vacuum at room temperature to obtain the bimetallic coordination metal-organic framework material.

Experiments and Tests:

A characterization of the bimetallic coordination metal-organic framework material (CoNi-dfdmt prepared in the Embodiment 6 is taken as an example):

As shown in FIG. 1, a crystal structure of CoNi-dfdmt has a molecular formula of $CoNiC_8H_4F_2S_2O_6$, which is a triclinic system and a P-1 space group. Where in a cell parameter, a=3.0220 Å, b=8.5157 Å, c=9.6597 Å, α=73.2086°, β=77.0605°, and γ=84.9539°. There are two octahedral coordination metal ions in the crystal structure: The coordination metal ions M1 are chelated with thiol and carboxyl, which is respectively four equator S atoms and two top O atoms; where M1-S has a bond length of 2.197 Å and 2.155 Å, and M1-O has a bond length of 1.830 Å. By sharing two opposite equatorial edges (i.e., $\eta^2$-S atoms spanning two metal ions), octahedrons arranged in a row and share opposite equatorial edges are formed along an A axis.

The octahedrons are integrated with the phenyl cell into a hybrid metal thiol salt layer for charge transport. Rest carboxyl O atoms (not coordinated with the coordination metal ions M1) protrudes on two sides of the hybrid metal thiol salt layer are bonded to two top ends of corresponding coordination metal ions M2. A bond length of M2-0 is 1.826 Å. The corresponding coordination metal ions M2 are further combined with four water molecules to form octahedral chains sharing edges of the M1 two-dimensional coordination network structure and embedded in the M1 two-dimensional coordination network structure. The octahedral chains do not fill an interlayer space, there are small channels between layers, and M2-O layers and interlayer gaps are configured as ion parts of the bimetallic coordination metal-organic framework material.

Figure 2:
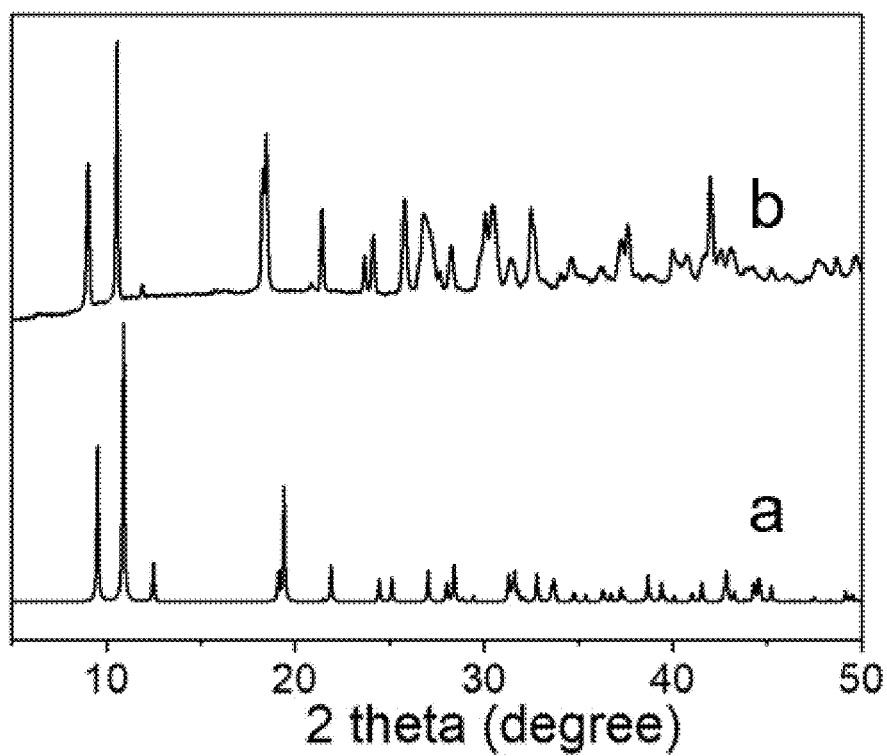
FIG. 2 is an X-ray powder diffractograms of the bimetallic coordination metal-organic framework material in the embodiment 6 of the present disclosure.

As shown in FIG. 2, it is noted that from a result of an X-ray powder diffraction test of CoNi-dfdmt, a diffraction spectrum of CoNi-dfdmt is highly consistent with an X-ray powder diffraction of a single crystal simulation at peak positions, which indicates that CoNi-dfdmt is pure phase. Further, according to the diffraction spectrum, it is indicated that diffraction peaks of CoNi-dfdmt are strong and sharp, and the synthesized coordination polymer CoNi-dfdmt is well crystalline. Moreover, contents of Co and Ni in CoNi-dfdmt are accurately determined by atomic absorption spectroscopy, and a molar ratio of Co to Ni is approximately 1:1.

Figure 3:
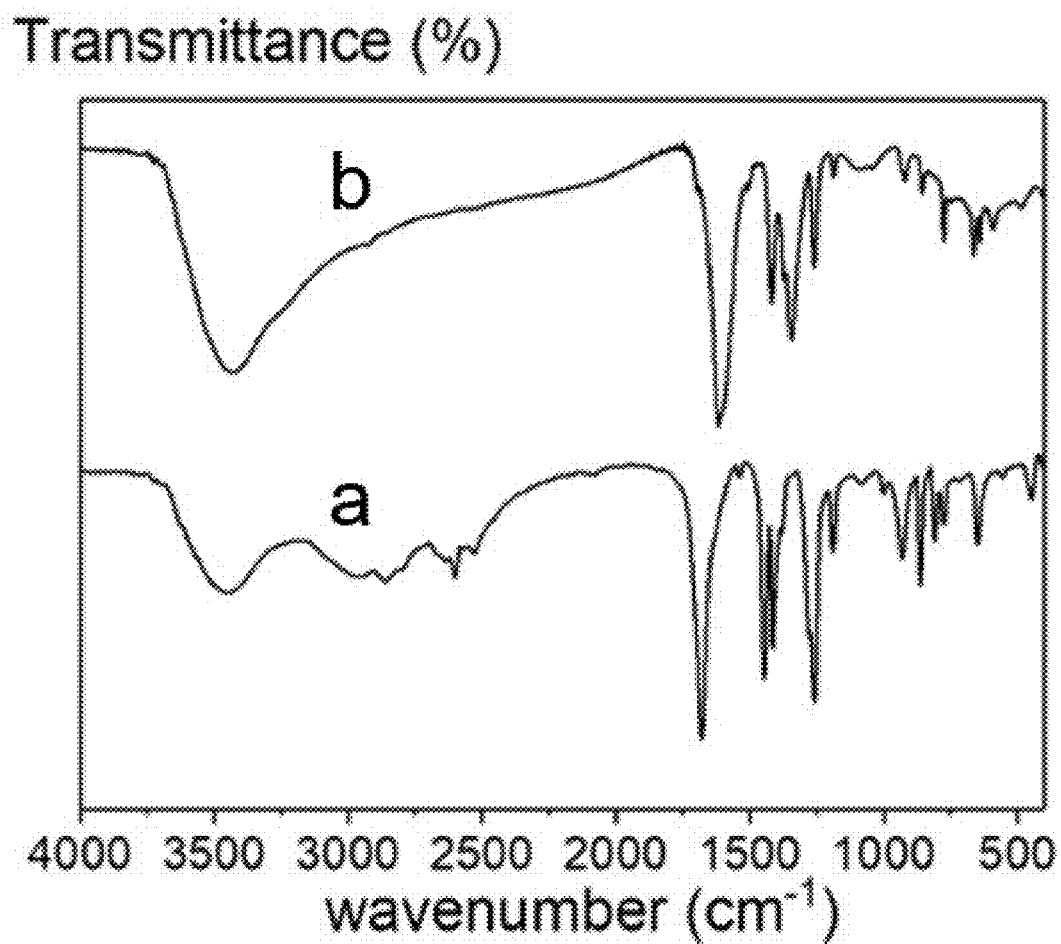
FIG. 3 is an infrared spectrum of the bimetallic coordination metal-organic framework material in the embodiment 6 of the present disclosure.

Referring to an infrared spectrum of CoNi-dfdmt and H4dfdmt as shown in FIG. 3, it is obvious that characteristic peaks of thiolat 2639 $cm^{-1}$ and 2542 $cm^{-1}$ in the ligands of $H_4$dfdmt disappeared, and a characteristic peak of the carbonyl group is shifted from 1682 $cm^{-1}$ to 1545 $cm^{-1}$, indicating that thiol and carboxylic acid functional groups in the ligands are coordinated with the cobalt or the nickel and the successful assembly of the coordination polymer CoNi-dfdmt.

Figure 6:
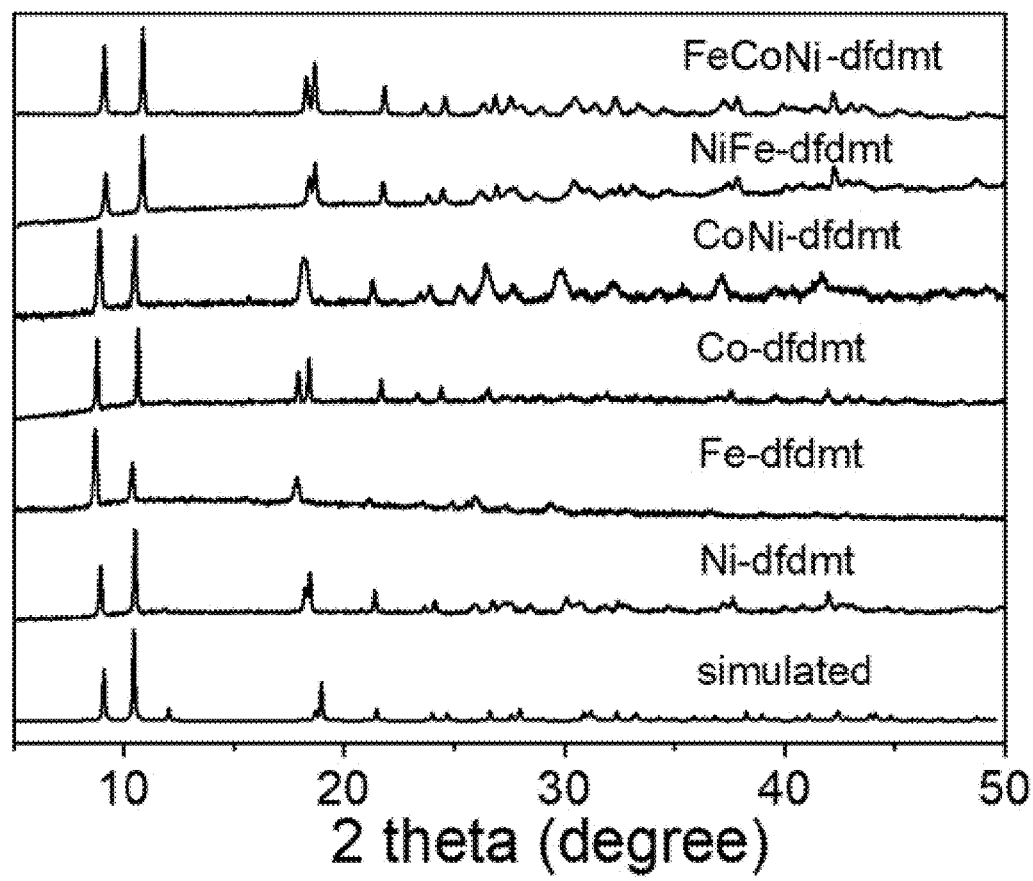
FIG. 6 is an X-ray powder diffractograms of the bimetallic coordination metal-organic framework material in embodiments 3, 5, 6 and 10-12 of the present disclosure.
Figure 7:
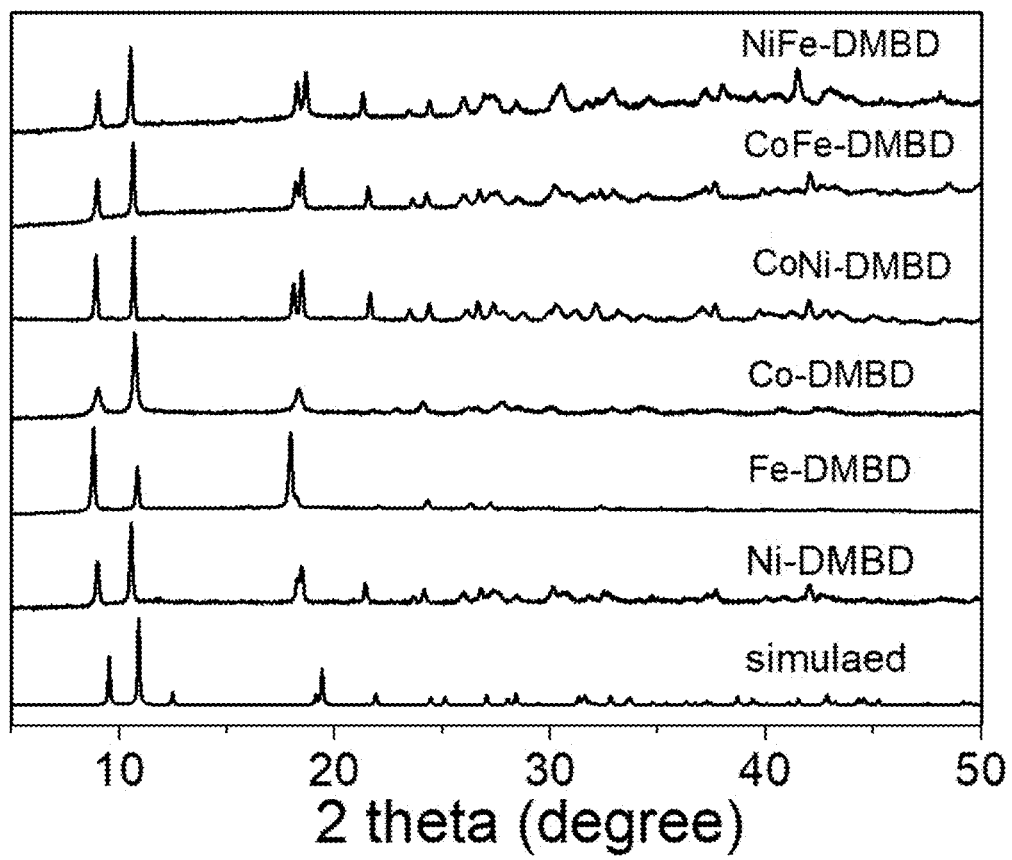
FIG. 7 is an X-ray powder diffractograms of the bimetallic coordination metal-organic framework material in embodiments 2, 4, 7-9, and 13 of the present disclosure.

Referring to FIGS. 6 and 7, it is indicated that the bimetallic coordination metal-organic framework material is assembled by organic ligands such asH4dfdmt and H$_4$DMBD, monometal such as iron, cobalt, and nickel or with plural metallic mixture such as cobalt-iron, cobalt-nickel, and iron-nickel.

The bimetallic-coordinated metal-organic framework material has bimetallic coordination centers, has the covalent charge carrier layer that can be applied in inorganic superconducting materials, and has the ionic layer for charge transport and charge storage, so the bimetallic-coordinated metal-organic framework materials of the present invention have been used in superconducting materials, conductive materials, semiconductor materials, or electromagnetic materials. and research of superconductivity, conductivity, and magnetism of the bimetallic-coordinated metal-organic framework material are carried out.

Figure 4:
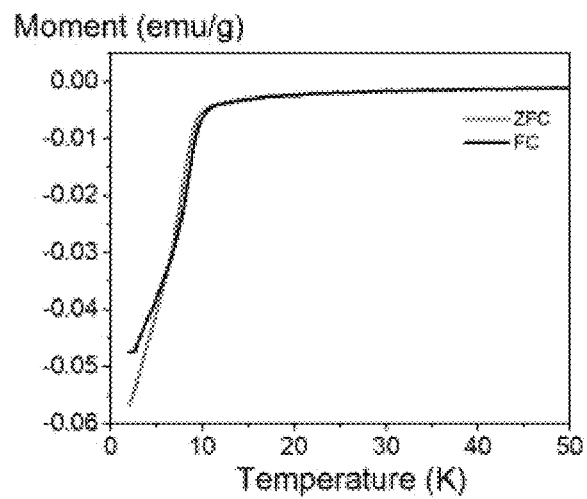
FIG. 4 is a graph showing a variation of magnetization with temperature of the bimetallic coordination metal-organic framework material in the embodiment 6 of the present disclosure.

Magnetic research: 10 mg of CoNi-dfdmt is weighed in a specific capsule and a relevant magnetic test is performed by a physical property measurement system (PPMS), and a result thereof is shown in FIG. 4.

It can be seen from FIG. 4 that CoNi-dfdmt starts to repel magnetic fields at 9 K, exhibiting antiferromagnetism, i.e., the Meissner effect, which shows another important property of the superconducting materials.

Figure 5:
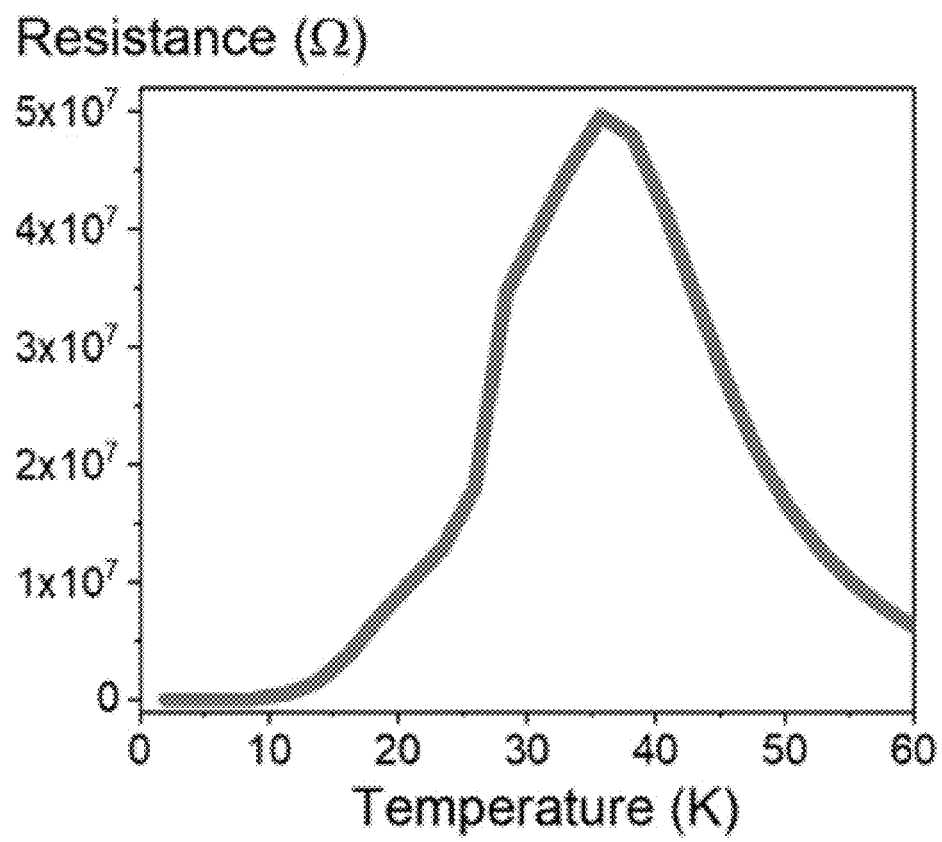
FIG. 5 is a graph showing a variation of resistance with temperature of the bimetallic coordination metal-organic framework material in the embodiment 6 of the present disclosure.

Conductivity study: 10 mg of CoNi-dfdmt is weighed and is received in a mold and pressed for 30 minutes at a pressure of 0.5 T by a tablet press machine to obtain a wafer with a certain thickness (with a diameter of 3 mm). Two circular surfaces of the wafer are connected with a thin gold wire and are coated with a layer of conductive silver paste. Ensuring that the thin gold wire tightly contacts with the two surfaces of the wafer, and then a curve of a resistance of the wafer with temperature is measured by the PPMS, and results are shown in FIG. 5.

Therefore, in the bimetallic coordination metal-organic framework material of the present disclosure, the carboxyl groups and the soft groups of the ligands are coordinated with the coordination metal ions to assemble the structure having space and the functions divided into the covalent charge carrier layers and the charge storage ion layers. Further, through the conjugation effect, functions of the covalent charge carrier layers and the charge storage ion layers of the ligands are enhanced, making a distance of electronic coupling action between metal centers of coordination metal ions is close, so the bimetallic coordination metal-organic framework material has unique electromagnetic properties and exhibits good electrical conductivity and magnetic coupling performance. Thus, the bimetallic coordination metal-organic framework material is used as the superconducting materials, the conductive materials, the semiconductor materials, or the electromagnetic materials.

The above embodiments are only optional embodiments of the present disclosure and cannot be used to limit the protection scope of the present disclosure. Any non-substantial changes and substitutions made by those skilled in the art on the basis of the present disclosure should fall within the protection scope of the present disclosure.

What is claimed is:

1. A bimetallic coordination metal-organic framework material, comprising:
    an M1 two-dimensional coordination network structure comprising M1 coordination layers; and
    M2 coordination structures embedded between the M1 coordination layers;
    wherein coordination metal ions M1 are coordinated with ligands to form the M1 two-dimensional coordination network structure; each of the M2 coordination structures is a zero-dimensional M2 coordination structure, a one-dimensional M2 coordination structure, or a two-dimensional M2 coordination structure; coordination metal ions M2 are coordinated with the ligands to form the M2 coordination structures;
    wherein each of the ligands is a compound containing a carboxyl group and soft groups; the coordination metal ions M1 form a M1 two-dimensional coordination network structure with the soft groups or form the M1 two-dimensional coordination network structure with the soft groups and carboxyl groups of the ligands; the coordination metal ions M2 and oxygen atoms of the carboxyl groups of the ligands form the M2 coordination structures embedded between the M1 coordination layers;
    wherein the soft groups are —XH, and X is selected from S and Se.

2. The bimetallic coordination metal-organic framework material according to claim 1, wherein the M2 coordination structures comprise one or more of H2O, hydroxide, and halogen.

3. The bimetallic coordination metal-organic framework material according to claim 1, wherein the coordination metal ions M1 are same as or different from the coordination metal ions M2; the coordination metal ions M1 and the coordination metal ions M2 are selected from one or more of transition metal ions, Ga, In, Sn, Tl, Pb, and Bi.

4. The bimetallic coordination metal-organic framework material according to claim 1, wherein the ligands are an aromatic compound, the carboxyl group and the soft groups of each of the ligand are directly or indirectly connected to an aromatic ring.

5. The bimetallic coordination metal-organic framework material according to claim 4, wherein each of the ligands comprises at least one carboxyl group and at least two soft groups.

6. A preparing method for the bimetallic coordination metal-organic framework material according to claim 1, comprising following steps:
    S11: weighing the ligands and metal salt, and adding the ligands and the metal salt into a container;
    S12: adding a mixed solution containing water and an organic solvent into the container, and sealing the container; and
    S13: placing the container in an oven and heating to obtain the bimetallic coordination metal-organic framework material.

7. The preparing method for the bimetallic coordination metal-organic framework material according to claim 6, wherein replacing the metal salt in the step S11 with a metal oxide; wherein the preparing method further comprises steps of preparing a metal oxide suspension:
    S21: dissolving the metal salt in the water to obtain a solution A, and dissolving NaBH$_4$ in the water to obtain a solution B; then adding the solution B into the solution A for reaction; and centrifuging, washing, and vacuum drying a product after reaction to obtain a metal oxide nanosheet; and
    S22: dispersing the metal oxide nanosheet prepared in the step S21 in the water to obtain the metal oxide suspension;
    wherein the container is a reaction kettle; when preparing the bimetallic coordination metal-organic framework material, the ligands are weighed and added into the reaction kettle together with the mixed solution containing the water and the organic solvent; the metal oxide suspension prepared in the step S22 is added into the reaction kettle, and a solvothermal reaction is performed to obtain the bimetallic coordination metal-organic framework material.

8. The preparing method for the bimetallic coordination metal-organic framework material according to claim 6, wherein in the mixed solution containing the water and the organic solvent, the organic solvent is selected from one or more of N,N-Dimethylformamide (DMF), N,N-diethylformamide (DEF), and ethanol (EtOH); wherein a volume ratio of the organic solvent to the water is 1: 2-8;
- wherein when the mixed solution is added, a regulator is simultaneously added; and the regulator is selected from one or more of formic acid, acetic acid, and trifluoroacetic acid;
- wherein a molar ratio of the ligands to metal ions of the metal salt is 1: 2.5-4.

9. An application of the bimetallic coordination metal-organic framework material according to claim 1, wherein the bimetallic coordination metal-organic framework material is applied in superconducting materials, conductive materials, semiconductor materials, or electromagnetic materials.

\* \* \* \* \*